(12) United States Patent
Utsugi

(10) Patent No.: US 6,911,571 B2
(45) Date of Patent: Jun. 28, 2005

(54) BANDAGE PAD FOR CHEMICAL PEELS

(75) Inventor: Ryuichi Utsugi, Tokyo (JP)

(73) Assignee: DRDC Limited, Tokyo (JP)

( * ) Notice: Subject to any disclaimer, the term of this patent is extended or adjusted under 35 U.S.C. 154(b) by 140 days.

(21) Appl. No.: 10/226,216

(22) Filed: Aug. 23, 2002

(65) Prior Publication Data

US 2004/0039323 A1 Feb. 26, 2004

(51) Int. Cl.[7] ................................................ A61F 13/00
(52) U.S. Cl. .......................... 602/58; 602/48; 602/54; 602/59; 604/304
(58) Field of Search ................................ 424/443–449; 604/304–308, 290; 602/41–59; 128/888, 889; D24/189

(56) References Cited

U.S. PATENT DOCUMENTS 4,413,621 A * 11/1983 McCracken et al. .......... 602/52
5,354,328 A * 10/1994 Doan et al. .................. 607/129
6,297,422 B1 * 10/2001 Hansen et al. ................. 602/57

FOREIGN PATENT DOCUMENTS

JP          10194925 A  *  7/1998  ............ A61K/7/00

* cited by examiner

Primary Examiner—Kim M. Lewis
(74) Attorney, Agent, or Firm—Michael Bednarek; Pillsbury Winthrop Shaw Pittman LLP

(57) ABSTRACT

To provide a bandage pad for chemical peels that is designed to be stuck on the skin so that the condition of the skin is visually checked while the bandage pad is staying on the skin. A bandage pad for chemical peels comprises a transparent silicone film backing and a chemical peeling agent spread over the entire surface of one side of the film backing. Grooves are formed in the surface of the film backing in both vertical and horizontal directions to define a matrix of small divisions. The divisions are easily separable from each other. When undesirable reactions are observed on the skin, only the division corresponding to the affected site of the skin can be removed immediately.

42 Claims, 2 Drawing Sheets

BANDAGE PAD FOR CHEMICAL PEELS

BACKGROUND OF THE INVENTION

The present invention relates to chemical peel that is used to improve the appearance of the skin by reducing roughness or dryness, treat acne and scars, reduce fine lines and wrinkles, and improve coloration by reducing age spots and other skin blemishes (e.g., skin pigmentation such as senile lentigo). More particularly, the present invention relates to a bandage pad for chemical peels for applying a chemical peeling agent to the skin of a wearer in chemical peels.

People have been using more and more cosmetic preparations with a low content of a chemical peeling agent, such as α-hydroxy acid (AHA), that improves the condition of the skin and that is effective for removing fine lines, wrinkles and freckles. Removal of fine lines, wrinkles, and freckles has been established as a medical field in western countries. In Japan, necessity for such treatments has been recognized in recent years. Studies on the treatments from a medical standpoint are being conducted widely with a surge in recognition.

Treatment of skin using a chemical peeling agent is typically called "chemical peel". Chemical peels are performed with chemical peeling agents such as trichloroacetic acids (TCAs), phenols, and fruit acids (e.g., α-hydroxy acids (AHAs)). The chemical peeling agent is applied to the skin as an aqueous solution at an appropriate concentration for a certain period of time. This results in a controlled chemical "burn" or "erosion" of the top layers of the skin. In other words, liquid chemicals as described above are applied to the skin to separate and peel off portions of the stratum corneum or the epidermis of the skin, which stimulates the production of new skin cells to treat the skin.

Chemical peel requires application of a chemical peeling agent to the skin at an appropriate concentration. Direct application of the chemical peeling agent to the skin of a wearer has, however, many problems in conjunction with formulation and operations of application. It tends to produce uncovered portions of the skin or result in uneven applications of the peeling agent. With this respect, a more convenient and easier application of the chemical peeling agent to the skin is considered that uses a bandage pad or a similar patch for chemical peels. Conventional bandage pads designed to stay on the skin for chemical peels have a backing made of fabric with a chemical peeling agent applied thereto.

Chemical peels typically stimulate regeneration of the skin by certain loading. Higher concentration of chemical peeling agents or unnecessarily longer contact with the chemical peeling agent may produce undesired effects on the skin such as inflammation and excessive denaturation of cells or proteins. The concentration of chemical peeling agents and the time interval for which a bandage pad for chemical peels is left on the skin to achieve the optimum result can be prescribed to a certain degree based on the experiments of an attending physician or results of preliminary tests. However, responses to therapeutic substances vary greatly from individual to individual. Even the response varies from day to day depending on, for example, the wearer's condition. It is significantly hard to make an exact prognosis of such responses.

Chemical peels may cause undesirable skin reactions, such as frosting (whitening due to the denaturation of superficial proteins), rash, or redness, on the skin of the wearer. If the wearer has such skin reactions, he or she should immediately discontinue the use of the treatment. In some cases, another agent should be applied to the skin to neutralize the peeling agent.

However, it is impossible to check the condition of the skin under the influence of the chemical peeling agent without removing the bandage pad for chemical peels when the bandage pad is not see-through. The impossibility of instantaneous checking of the influence on the skin tends to defer decision of interruption of treatment when chemical peels are performed excessively.

It is thus required that the bandage pad for chemical peels be able to provide an advantage for the application of peeling agents and allow physicians to monitor the condition of the skin during a therapeutic treatment in order to make the bandage pad more feasible and practical. A more widespread use of them cannot be achieved till the above-mentioned problems are solved.

For chemical peels, the chemical peeling agent should be applied so that all areas of the skin to be treated are covered evenly.

If frosting, rash, redness, or inflammation is caused on the skin of the wearer in treatment with a bandage pad for chemical peels, it is necessary to remove the bandage pad immediately. Complete removal of the bandage pad for chemical peels, however, turns out an interruption of treatment of areas where no inflammation is observed. In such a case, these areas are treated only insufficiently. It is difficult to treat all areas of the skin to be treated evenly with conventional bandage pads for chemical peels.

Therefore, an object of the present invention is to provide a practical bandage pad for chemical peels.

More specifically, the present invention is directed to provide a bandage pad for chemical peels that offers combined advantages of easier application and treatment of skin by chemical peels while monitoring the condition of the skin.

Another object of the present invention is to provide a bandage pad for chemical peels with which interruption of treatment or application of a neutralizing agent can be made immediately only at the site where undesirable reactions occur while continuing chemical peel of the remaining sites.

SUMMARY OF THE INVENTION

In order to solve the above-mentioned problems, a bandage pad for chemical peels according to the present invention comprises a see-through film backing; and a chemical peeling agent that is applied to one side of the film backing, the bandage pad being designed to be stuck on the skin of a wearer so that the condition of the skin is visually checked while the bandage pad is staying on the skin. With this type of the bandage pad for chemical peels, the surface of the skin is always visible through the film backing even when the skin is covered with the bandage pad for chemical peel procedures. Even when the chemical peel leads undesirable skin reactions, the reactions can be found promptly. Thus, interruption of the treatment and/or application of a neutralizing agent can be made timely. This contributes to improvement of safety of the chemical peels.

It is noted that portions that are see-through from either side or from only one side to the other of the film backing should be overlapped with the portions carrying the chemical peeling agent. The overlap may be located anywhere within the film backing. The whole film backing may be completely transparent or, alternatively, it may be see-through from only one side to the other.

The film backing of the bandage pad for chemical peels according to the present invention may be any film backing as long as the surface of the skin is visible through the bandage pad staying on the skin. The film backing may be completely transparent. Alternatively, it may be translucent, semi-transparent, or even clear-colored to the extent that the condition of the skin can be visually checked. The film backing may be either single-layered or multi-layered as long as the surface of the skin is visible through the bandage pad stuck on the skin. For example, the film backing may comprise a layer to keep the shape of the film backing and a layer where chemical peeling agent can be held. In addition, the film backing may be formed as a sheer mesh of a non-transparent or opaque material as long as the condition of the skin can be visually checked without removing the bandage pad from the skin. The film backing may include one or more layers in addition to the sheer mesh layer.

The film backing may have adhesiveness on the above-mentioned one side. This allows the film backing to stay on the skin of a wearer without the aid of something. Of course, the film backing may be put on the skin with an adhesive strip or any other similar material, but the adhesiveness on the film backing would provide more convenient use. The film backing may be made of a sticky material or an adhesive may be applied to a certain portion of the non-sticky film backing. The adhesive may be applied to other portion(s) than where the chemical peeling agent is applied. Alternatively, the adhesive may be mixed with the chemical peeling agent for application purposes.

The film backing may be flexible and conform to the body of a wearer. The flexible film backing fits the skin and moves with the wearer. This makes it possible to contact the chemical peeling agent with the skin, even for hard-to-fit areas.

For a see-through film backing, it may be made of silicone. Silicone is a clear material that has the capacity to be formed into various shapes with different surface properties depending on a processing method used. Accordingly, silicone materials are well suitable for the film backing of the present invention. For example, a silicone material is formed into a film with one surface having adhesion and the other surface having rigidity like a cured resin. A chemical peeling agent is applied to the sticky surface. This provides a single-layered film backing, simplifying the configuration of the bandage pad for chemical peels.

The film backing of the bandage pad for chemical peels according to the present invention may be configured so that a part of the film backing can be separated easily. When chemical peel results in undesirable skin reactions, the portion of the film backing that corresponds to the affected area is separated immediately to minimize influences to the skin. On the other hand, the chemical peel may be performed continuously for a desired period of time on the remaining portions where no skin reaction is observed. The easy-to-cut bandage pad may preferably be separated with fingers, without using any other tools.

The film backing of the bandage pad for chemical peels according to the present invention may be previously marked off into small divisions, the division being arranged continuously but easily separable from each other to allow a given division to be removed when necessary. By marking off the film backing into these small divisions, the film backing can be removed easily only at the portion on the skin having undesirable reactions while remaining on other portions.

The small divisions are separated from each other by, for example, perforations. Alternatively, the divisions may be separated by grooves that do not penetrate through the film backing. The small divisions of the bandage pad for chemical peels according to the present invention may have any one of suitable shapes. For example, the film backing may be marked off into a matrix of small divisions.

The film backing may include, on one side thereof, keeper means that is suitable for keeping chemical peeling agents. The keeper means may be, for example, cotton, hydrogels, and agar-like materials.

In the bandage pad for chemical peels as described above, the chemical peeling agent is not necessarily provided already applied to the film backing. Bandage strips with no chemical peeling agent require a bit more effort because a chemical peeling agent should be applied before use. However, such bandage strips have a similar advantage to that of the above-mentioned bandage pad for chemical peels from the viewpoint that the skin can be protected from excessive chemical peels. For example, a bandage pad for chemical peels may include a film backing that is see-through from either side or from only one side to the other; and keeper means that is provided on one side of the film backing to keep chemical peeling agents, the bandage pad being designed to be stuck on the skin of a wearer so that the condition of the skin is visually checked while the bandage pad is staying on the skin. It is noted that portions that are see-through from either side or from only one side to the other of the film backing are only required to be overlapped with the portions to which a chemical peeling agent is to be applied. The whole film backing may be see-through from either side or from only one side to the other of the film backing.

DETAILED DESCRIPTION OF THE PREFERRED EMBODIMENTS

Figure 1:
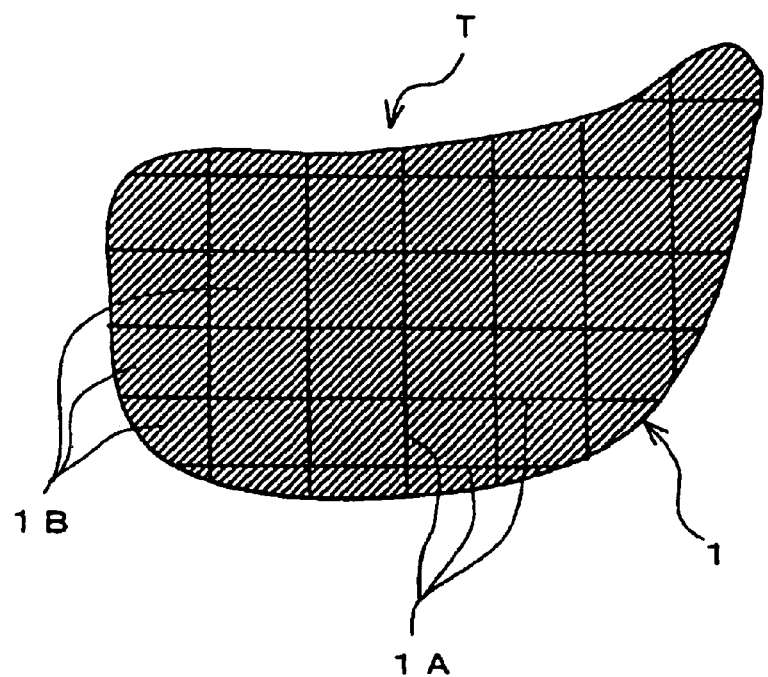
FIG. 1 is a plane view showing an appearance of a bandage pad for chemical peels according to an embodiment of the present invention.

Referring to the drawings, a preferred embodiment of a bandage pad for chemical peels according to the present invention is described.

Figure 2:
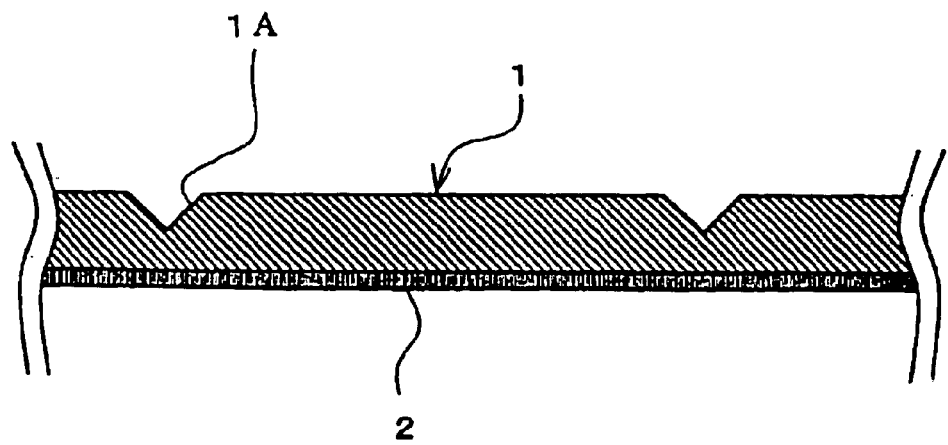
FIG. 2 is a cross-sectional view of the bandage pad for chemical peels shown in FIG. 1, taken along the thickness thereof.

FIG. 1 is a plane view showing an appearance of a bandage pad for chemical peels T according to this embodiment. FIG. 2 shows a cross-section of the bandage pad. The bandage pad for chemical peels T in this embodiment comprises a film backing 1 and a chemical peeling agent 2. The film backing 1 is made of silicone so that the film backing 1 is see-through to a certain extent. The chemical peeling agent 2 is spread over a given area, such as the entire surface, of one side of the film backing 1.

A combination of the film backing 1 and the chemical peeling agent 2 may be formed in the form of a bandage patch, pack or strip depending on the site to which the chemical peel is applied. Further, the chemical peeling agent 2 is not required to be on the film backing 1 at the time of manufacture or delivery. A wearer may spread the chemical peeling agent 2 over the film backing 1 before use to prepare the bandage pad.

The film backing 1 in this embodiment contours the cheek of a human. The shape of the film backing 1 is not specifically limited. For example, the film backing 1 may be shaped like a face mask, leaving openings around eyes, mouth and nostrils. Alternatively, the film backing 1 may be a narrow strip of, for example, 2 cm width.

The back surface of the film backing 1 in this embodiment (to which the chemical peeling agent 2 is applied) may be treated to provide certain adhesion. This allows the film backing 1 to keep the chemical peeling agent 2 on the back side thereof. The top surface of the film backing 1 (opposite to the surface carrying the chemical peeling agent 2) is less sticky. It is similar to a surface of the plastic film for easier handling of the bandage pad for chemical peels T.

The back surface of the bandage pad for chemical peels may be covered with a protective release liner so that the bandage pad can be removed easily from the liner. The protective release liner prevents evaporation of the chemical peeling agent 2 and/or moisture.

Grooves 1A are formed in the surface of the film backing 1 in vertical and horizontal directions. Each groove 1A has the depth smaller than the thickness of the film backing 1 so that the grooves 1A do not penetrate through the film backing 1. The grooves 1A define rectangular divisions 1B on the film backing 1. The sides of the divisions 1B may be, for example, 0.5 to 2 cm in length depending on the site to be subjected to chemical peels. Each division 1B in this embodiment is a 1-cm square but the size of the divisions 1B is not specifically limited.

In this embodiment, the film backing 1 is marked off into a matrix of the divisions 1B by the grooves 1A that are formed along the boundaries of the divisions 1B.

As described above, the film backing 1 made of silicone can be easily separated with fingers. The grooves 1A ensure removal of a given division when necessary without undesirably breaking off the film backing 1. In this context, some or all grooves 1A may be replaced with perforations to define the divisions 1B.

The chemical peeling agent 2 contains at least one of the following: glycolic acid, fruit acid (α-DHA), TCA, phenol, lactic acid, salicylic acid, maleic acid, mandelic acid, ethyl pyruvate, glutaric acid, methyl pyruvate, pyruvic acid, tartaric acid, tartonic acid, glyoxylic acid, glycolate ethyl, succinic acid, tretinoin, formic acid, α-hydroxyoctanoic acid, decanoic acid, and acetic acid. The chemical peeling agent 2 may be selected depending on applications and/or suitability for a wearer. Although the chemical peeling agent 2 that is used for the bandage pad for chemical peels T in this embodiment is glycolic acid, there is no limitation for the chemical peeling agents for the purpose of the present invention.

The chemical peeling agent 2 may contain, for example, from 1% to 50% of TCA and from 1% to 75% of glycolic acid. Other ingredients may optionally be added.

The level of the glycolic acid is variable. For medical applications, the bandage pad for chemical peels may be used for all pH ranges. For facial treatments or other beauty purposes, the glycolic acid may be present in a pH range 2.5–3.5. For domestic use, the glycolic acid may be contained at a pH of 3.5 or higher. Thus, strength of chemical peeling agents should be adjusted by the safety considerations, depending on specific applications. Chemical peeling agents at a higher pH than 2.5 produce a smaller effect but are much more safer. A lower pH than 2.5 is more effective but has a larger risk of causing inflammation.

The film backing 1 may be made of a non-sticky material. In such a case, an adhesive may be applied to the back surface of the film backing 1. With this configuration, the adhesive may be applied to the back side of the film backing 1 along with the chemical peeling agent 2 as described above. For example, a mixture of the chemical peeling agent 2 and an adhesive may be spread over the back surface of the film backing 1. The adhesive serves as the keeper means of the present invention. The adhesive may be applied to the portions of the back surface of the film backing 1 that correspond to the above-mentioned grooves 1A, and the chemical peeling agent 2 may be applied to other portions. In such a case, the adhesive is applied along the peripheries of the divisions 1B and the remaining portions on the back side are covered with the chemical peeling agent 2. Patterns of applying the adhesive and the chemical peeling agent 2 may be determined depending on, for example, the shape of the film backing 1 and on whether the film backing 1 is marked off into the divisions 1B. It should be noted that the adhesive may be eliminated and the film backing 1 is not made sticky. Alternatively, another means such as an adhesive tape is used to secure the film backing 1 to the skin. No adhesion is required for the bandage pad for chemical peels when it is used at rest.

Figure 3:
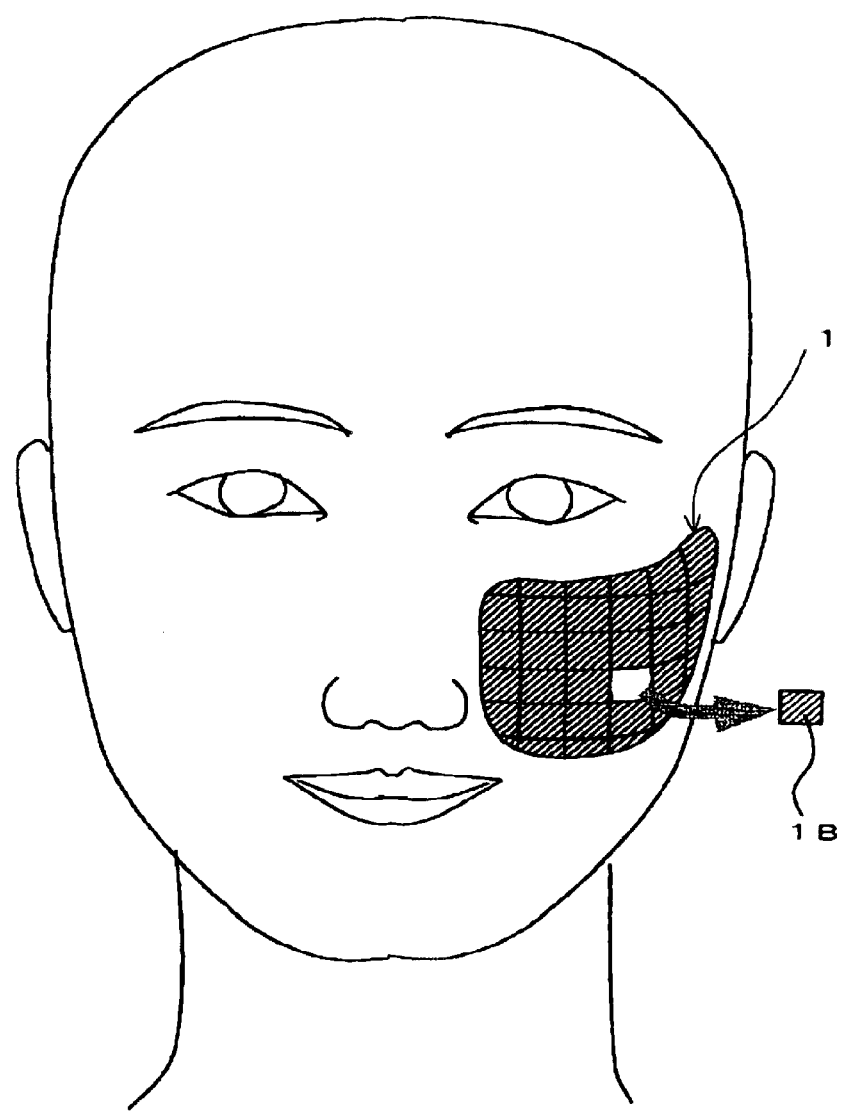
FIG. 3 is a perspective view illustrating how to use the bandage pad for chemical peels shown in FIG. 1.

How to use the bandage pad for chemical peels T is described as an example. The bandage pad for chemical peels T is placed at a predetermined site on the skin of a person to be subjected to the chemical peels. The bandage pad for chemical peels T according to this embodiment is to be placed on the cheek of a person as shown in FIG. 3. Since the back surface of the film backing 1 in this embodiment is somewhat sticky, the bandage pad for chemical peels T can be secured to the skin without using an adhesive material.

When the bandage pad for chemical peels T is placed on the skin, the chemical peeling agent 2 on the back side thereof acts upon the skin. The see-through feature of the film backing 1 allows visual observation of the skin with the bandage pad for chemical peels T staying on the skin.

When undesirable skin reactions occur due to, for example, a higher concentration of the chemical peeling agent 2, the division 1B over the affected site is removed. This can be achieved easily with bare hands for the above-mentioned grooves 1A. In this way, the chemical peel is terminated immediately after any undesirable reactions occur at the affected site. For other sites, the chemical peel can be continued.

A neutralizing agent to neutralize the chemical peeling agent may be applied to the exposed portion of the skin, from which the division 1B has been removed, in order to minimize the undesirable reactions when necessary for some reasons such as excessive skin reactions. The neutralizing agent may be directly applied to the affected site. Alternatively, a small piece or strip having the same dimension as the division 1B may be prepared and the neutralizing agent may previously be applied on one side thereof to place the piece or strip on the portion of the exposed skin after the removal of the division 1B.

The above-mentioned embodiment is for a case where the chemical peeling agent 2 is directly applied to the film backing 1 on one side thereof. A modified version may comprise a keeper means that is suitable for keeping the chemical peeling agent on one side of the film backing 1. The chemical peeling agent 2 is carried on the film backing 1 by means of the keeper means. The keeper means may be an adhesive, or alternatively, a cotton, a hydrogel, or an agar-like material. The keeper means may be impregnated with a solution or a gel of the chemical peeling agent 2 to keep the chemical peeling agent 2. For example, a thin cotton gauze may be dipped into a solution or a gel of the chemical peeling agent 2 to saturate the gauze with the agent. In such a case, the keeper means is larger than the film backing 1 in thickness to a certain degree. This is because a thinner keeper means produces gaps between the bandage pad and the skin when the bandage pad is secured on the skin with the edges thereof being overlapped with the edges of the keeper means. With this respect, the keeper means made of a deformable material to have a certain thickness. The gaps are filled as a result of deformation of the keeper means. This prevents the gaps from being formed and allows uniform application of the chemical peeling agent to the skin over a predetermined range. For example, the keeper means is at least almost identical in thickness to the film backing 1. This eliminates production of gaps when the bandage pad is laminated with the keeper means for use.

What is claimed is:

1. A bandage pad for chemical peels comprising:
a transparent film backing; and
a chemical peeling agent that is applied to one side of said film backing, the bandage pad being designed to be stuck on the skin of a wearer so that the condition of the skin is visually checked while the bandage pad remains on the skin,
wherein said film backing is marked off into a matrix of small divisions, the divisions being arranged continuously but easily separable from each other to allow a given division to be removed when necessary.

2. The bandage pad as claimed in claim 1, wherein said film backing has a predetermined adhesion on the one side to allow said film backing to remain on the skin of a wearer without the aid of something.

3. The bandage pad as claimed in claim 2, wherein said film backing is configured so that a part of said film backing is easily separated from said film backing.

4. The bandage pad as claimed in claim 2, wherein the small divisions are separated from each other by perforations.

5. The bandage pad as claimed in claim 2, wherein the chemical peeling agent is applied to the one side of said film backing as a mixture with an adhesive that is used to keep said film backing to remain on the skin.

6. The bandage pad as claimed in claim 2, wherein said film backing has a predetermined adhesion on the one side to allow said film backing to remain on the skin of a wearer without the aid of something.

7. The bandage pad as claimed in claim 1, wherein said film backing is flexible and conforms to the body of a wearer.

8. The bandage pad as claimed in claim 7, wherein said film backing is configured so that a part of said film backing is easily separated from said film backing.

9. The bandage pad as claimed in claim 7, wherein the small divisions are separated from each other by perforations.

10. The bandage pad as claimed in claim 7, wherein the small divisions are separated from each other by grooves that do not penetrate through said film backing.

11. The bandage pad as claimed in claim 1, wherein said film backing is made of silicone.

12. The bandage pad as claimed in claim 11, wherein the small divisions are separated from each other by perforations.

13. The bandage pad as claimed in claim 11, wherein the small divisions are separated from each other by grooves that do not penetrate through said film backing.

14. The bandage pad as claimed in claim 1, wherein said film backing is configured so that a part of said film backing is easily separated from said film backing.

15. The bandage pad as claimed in claim 1, wherein the small divisions are separated from each other by perforations.

16. The bandage pad as claimed in claim 1, wherein the small divisions are separated from each other by grooves that do not penetrate through said film backing.

17. The bandage pad as claimed in claim 1, wherein the small divisions are separated from each other by grooves that do not penetrate through said film backing.

18. A bandage pad for chemical peels comprising:
a transparent film backing; and
a chemical peeling agent that is applied to one side of said film backing, the bandage pad being designed to be stuck on the skin of a wearer so that the condition of the skin is visually checked while the bandage pad remains on the skin,
wherein said film backing is marked off into small divisions, the divisions being arranged continuously but easily separable from each other to allow a given division to be removed when necessary, and
wherein said chemical peeling agent is applied to each of said small divisions.

19. The bandage pad as claimed in claim 18, wherein said film backing is flexible and conforms to the body of a wearer.

20. The bandage pad as claimed in claim 18, wherein said film backing is made of silicone.

21. The bandage pad as claimed in claim 18, wherein said film backing is configured so that a part of said film backing is easily separated from said film backing.

22. The bandage pad as claimed in claim 18, wherein said film backing has a predetermined adhesion on the one side to allow said film backing to remain on the skin of a wearer without the aid of something, and wherein said film backing is configured so that a part of said film backing is easily separated from said film backing.

23. The bandage pad as claimed in claim 18, wherein the small divisions are separated from each other by perforations.

24. The bandage pad as claimed in claim 18, wherein the small divisions are separated from each other by grooves that do not penetrate through said film backing.

25. The bandage pad as claimed in claim 18, wherein said film backing has a predetermined adhesion on the one side to allow said film backing to remain on the skin of a wearer without the aid of something; and
wherein the small divisions are separated from each other by perforations.

26. The bandage pad as claimed in claim 18, wherein said film backing has a predetermined adhesion on the one side to allow said film backing to remain on the skin of a wearer without the aid of something, and
wherein the small divisions are separated from each other by grooves that do not penetrate through said film backing.

27. The bandage pad as claimed in claim 18, wherein said film backing is flexible and conforms to the body of a wearer, and
wherein the small divisions are separated from each other by perforations.

28. The bandage pad as claimed in claim 18, wherein said film backing is flexible and conforms to the body of a wearer; and
wherein the small divisions are separated from each other by grooves that do not penetrate through said film backing.

29. The bandage pad as claimed in claim 18, wherein said film backing is made of silicone, and wherein the small divisions are separated from each other by perforations.

30. The bandage pad as claimed in claim 18, wherein said film backing is made of silicone, and
wherein the small divisions are separated from each other by grooves that do not penetrate through said film backing.

31. The bandage pad as claimed in claim 18, wherein said film backing is flexible and conforms to the body of a wearer, and
wherein the chemical peeling agent is applied to the one side of said film backing as a mixture with an adhesive that is used to keep said film backing to remain on the skin.

32. A bandage pad for chemical peels comprising:
a film backing that is see-through from only one side to the other; and
a chemical peeling agent that is applied to either side of said film backing, the bandage pad being designed to be stuck on the skin of a wearer so that the condition of the skin is visually checked while the bandage pad remains on the skin,
wherein said film backing is marked off into a matrix of small divisions, the divisions being arranged continuously but easily separable from each other to allow a given division to be removed when necessary.

33. The bandage pad as claimed in claim 32, wherein said film backing is flexible and conforms to the body of a wearer, and wherein said film backing is configured so that a part of said film backing is easily separated from said film backing.

34. A bandage pad for chemical peels comprising:
a film backing that is see-through from only one side to the other; and
a chemical peeling agent that is applied to either side of said film backing, the bandage pad being designed to be stuck on the skin of a wearer so that the condition of the skin is visually checked while the bandage pad remains on the skin,
wherein said film backing is marked off into small divisions, the divisions being arranged continuously but easily separable from each other to allow a given division to be removed when necessary, and
wherein said chemical peeling agent is applied to each of said small divisions.

35. A bandage pad for chemical peels comprising:
a see-through film backing; and
keeper means that is provided on one side of said film backing for keeping a chemical peeling agent, the bandage pad being designed to be stuck on the skin of a wearer so that the condition of the skin is visually checked while the bandage pad remains on the skin,
wherein said film backing is marked off into a matrix of small divisions, the divisions being arranged continuously but easily separable from each other to allow a given division to be removed when necessary.

36. The bandage pad as claimed in claim 35, wherein said keeper means is one of cotton, hydrogel, and an agar-like material.

37. A bandage pad for chemical peels:
a see-through film backing; and
keeper means that is provided on one side of said film backing for keeping a chemical peeling agent, the bandage pad being designed to be stuck on the skin of a wearer so that the condition of the skin is visually checked while the bandage pad remains on the skin,
wherein said film backing is marked off into small divisions, the divisions being arranged continuously but easily separable from each other to allow a given division to be removed when necessary, and
wherein said keeper means is provided on each of said small divisions.

38. The bandage pad as claimed in claim 37, wherein said keeper means is one of cotton, hydrogel, and an agar-like material.

39. A bandage pad for chemical peels comprising:
a film backing that is see-through from only one side to the other; and
keeper means that is provided on one side of said film backing for keeping a chemical peeling agent, the bandage pad being designed to be stuck on the skin of the wearer so that the condition of the skin is visually checked while the bandage pad remains on the skin,
wherein said film backing is marked off into a matrix of small divisions, the divisions being arranged continuously but easily separable from each other to allow a given division to be removed when necessary.

40. The bandage pad as claimed in claim 39, wherein said keeper means is one of cotton, hydrogel, and an agar-like material.

41. A bandage pad for chemical peels comprising:
a film backing that is see-through from only one side to the other; and
keeper means that is provided on one side of said film backing for keeping a chemical peeling agent, the bandage pad being designed to be stuck on the skin of the wearer so that the condition of the skin is visually checked while the bandage pad remains on the skin,
wherein said film backing is marked off into small divisions, the divisions being arranged continuously but easily separable from each other to allow a given division to be removed when necessary, and
wherein said keeper means is provided on each of said small divisions.

42. The bandage pad as claimed in claim 41, wherein said keeper means is one of cotton, hydrogel, and an agar-like material.

* * * * *